US012036363B2

(12) United States Patent
Putman et al.

(10) Patent No.: US 12,036,363 B2
(45) Date of Patent: Jul. 16, 2024

(54) RESPIRATORY PATTERN ANALYSIS DURING VARIABLE POSITIVE AIR PRESSURE DELIVERY FOR SPONTANEOUSLY BREATHING PATIENTS

(71) Applicant: Nanotronics Health, LLC., Brooklyn, NY (US)

(72) Inventors: John B. Putman, Celebration, FL (US); Matthew C. Putman, Brooklyn, NY (US); Julie A. Orlando, Copley, OH (US)

(73) Assignee: Nanotronics Health, LLC., Brooklyn, NY (US)

( * ) Notice: Subject to any disclaimer, the term of this patent is extended or adjusted under 35 U.S.C. 154(b) by 0 days.

(21) Appl. No.: 17/660,243

(22) Filed: Apr. 22, 2022

(65) Prior Publication Data
US 2023/0338680 A1  Oct. 26, 2023

(51) Int. Cl.
*A61M 16/00* (2006.01)
*G16H 20/40* (2018.01)
*G16H 40/63* (2018.01)

(52) U.S. Cl.
CPC .... *A61M 16/0069* (2014.02); *A61M 16/0003* (2014.02); *A61M 16/0051* (2013.01);
(Continued)

(58) Field of Classification Search
CPC .......... A61M 16/0069; A61M 16/0003; A61M 16/0051; A61M 16/024
See application file for complete search history.

(56) References Cited

U.S. PATENT DOCUMENTS 9,789,273 B2   10/2017  Lucci et al.
11,672,933 B1   6/2023  Putman et al.
(Continued)

FOREIGN PATENT DOCUMENTS

CN   102186522   9/2011
CN   102397616   4/2012
(Continued)

OTHER PUBLICATIONS

PCT International Application No. PCT/US22/25611, International Search Report and Written Opinion of the International Searching Authority, dated Jul. 27, 2022, 9 pages.
(Continued)

*Primary Examiner* — Margaret M Luarca
(74) *Attorney, Agent, or Firm* — DLA PIPER LLP (US)

(57) ABSTRACT

A positive airway pressure device includes a blower, a chamber, a sensor, and a controller. The controller is configured to perform operations. The operations include determining a baseline respiratory response for a patient. The operations further include initializing the blower to deliver a therapy pressure to the patient. The operations further include receiving, from the sensor, real-time respiratory response data while delivering therapy to the patient. The operations further include analyzing the real-time respiratory response data to determine whether a sleep disruption has occurred by comparing the real-time respiratory response data to the baseline respiratory response for the patient. The operations further include, based on the analyzing, determining that a sleep disruption has occurred based on an anomaly detected in the real-time respiratory response data. The operations further include, based on the determining, initiating an action to account for the sleep disruption.

12 Claims, 12 Drawing Sheets

(52) U.S. Cl.
CPC .......... *A61M 16/024* (2017.08); *G16H 20/40* (2018.01); *G16H 40/63* (2018.01); *A61M 2016/0027* (2013.01)

(56) References Cited

U.S. PATENT DOCUMENTS

| | | |
|---|---|---|
| 2002/0014239 A1 | 2/2002 | Chalvignac |
| 2003/0223877 A1 | 12/2003 | Anstine et al. |
| 2005/0005937 A1 | 1/2005 | Farrugia et al. |
| 2006/0272642 A1 | 12/2006 | Chalvignac |
| 2007/0016093 A1 | 1/2007 | Rapoport et al. |
| 2009/0101148 A1 | 4/2009 | Cha et al. |
| 2010/0078024 A1 | 4/2010 | Andrieux et al. |
| 2010/0258123 A1 | 10/2010 | Somaiya et al. |
| 2010/0313898 A1* | 12/2010 | Richard ............ A61M 16/0666 128/200.24 |
| 2010/0319691 A1 | 12/2010 | Lurie et al. |
| 2011/0209706 A1 | 9/2011 | Truschel et al. |
| 2013/0228180 A1 | 9/2013 | Ahmad et al. |
| 2013/0228181 A1 | 9/2013 | Ahmad et al. |
| 2013/0340758 A1 | 12/2013 | Schindhelm et al. |
| 2014/0069429 A1 | 3/2014 | Lucci et al. |
| 2014/0238398 A1 | 8/2014 | Christopher et al. |
| 2015/0007815 A1 | 1/2015 | Duquette et al. |
| 2015/0217079 A1 | 8/2015 | Mcauley et al. |
| 2015/0273176 A1 | 10/2015 | Acker et al. |
| 2016/0022938 A1* | 1/2016 | Rapoport ............ A61M 16/026 128/204.23 |
| 2016/0193438 A1 | 7/2016 | White et al. |
| 2016/0287824 A1 | 10/2016 | Chang |
| 2018/0236191 A1 | 8/2018 | Martin et al. |
| 2019/0175854 A1 | 6/2019 | Nakada et al. |
| 2020/0023156 A1* | 1/2020 | Miller .................. A61M 16/06 |
| 2020/0179629 A1 | 6/2020 | Burgess et al. |
| 2020/0268994 A1 | 8/2020 | Boulanger |
| 2020/0405986 A1 | 12/2020 | Brambilla et al. |
| 2021/0052839 A1 | 2/2021 | Li et al. |
| 2021/0187221 A1 | 6/2021 | Bassin |
| 2021/0213221 A1 | 7/2021 | Andersson et al. |
| 2021/0308400 A1 | 10/2021 | Sipes, Jr. et al. |
| 2022/0111166 A1 | 4/2022 | Peake et al. |

FOREIGN PATENT DOCUMENTS

| | | |
|---|---|---|
| CN | 102802709 | 11/2012 |
| CN | 111457963 | 7/2020 |
| CN | 112367914 | 2/2021 |
| TW | 201529112 | 8/2015 |
| TW | 202146069 | 12/2021 |
| WO | 2021107874 | 6/2021 |

OTHER PUBLICATIONS

PCT International Application No. PCT/US22/29147, International Search Report and Written Opinion of the International Searching Authority, dated Sep. 14, 2022, 16 pages.

Office Action from Taiwan Patent Application No. 111117616, dated May 22, 2023, 4 pages.

* cited by examiner

RESPIRATORY PATTERN ANALYSIS DURING VARIABLE POSITIVE AIR PRESSURE DELIVERY FOR SPONTANEOUSLY BREATHING PATIENTS

CROSS-REFERENCE TO RELATED APPLICATIONS

This application is related to U.S. patent application Ser. No. 17/659,971, filed Apr. 20, 2022, which claims priority to U.S. Provisional Application Ser. No. 63/292,288, filed Dec. 21, 2021, which are hereby incorporated by reference in their entireties.

FIELD OF DISCLOSURE

The present disclosure generally relates to a positive airway pressure system, and more specifically, to a system and method for delivering bi-level treatment to a patient using a positive airway pressure system

BACKGROUND

Non-invasive ventilation (NIV) is often used for patients experiencing respiratory destress. This may be prescribed for patients with Obstructive Sleep Apnea (OSA), Chronic obstructive pulmonary disorder (COPD), pneumonia or other respiratory disorders. NIV is often prescribed as supplying positive air pressure (PAP) to the patient by a face mask or other device such as nasal pillows. Depending upon the symptoms, the PAP may be either continuous positive air pressure (CPAP) or bi-level positive air pressure.

SUMMARY

In some embodiments, a positive airway pressure device is disclosed herein. The positive airway pressure device includes a blower, a chamber, a sensor, and a controller. The chamber is configured to receive gas generated by the blower and output the gas to a patient. The sensor is at least partially disposed in a gas pathway. The sensor is configured to measure a pressure in the chamber. The controller is in communication with the blower and the sensor. The controller is configured to perform operations. The operations include determining a baseline respiratory response for a patient by collecting, via the sensor, respiratory response data from the patient for a plurality of pressure levels. The operations further include initializing the blower to deliver a therapy pressure to the patient. The operations further include receiving, from the sensor, real-time respiratory response data while delivering therapy to the patient. The operations further include analyzing the real-time respiratory response data to determine whether a sleep disruption has occurred by comparing the real-time respiratory response data to the baseline respiratory response for the patient. The operations further include, based on the analyzing, determining that a sleep disruption has occurred based on an anomaly detected in the real-time respiratory response data. The operations further include, based on the determining, initiating an action to account for the sleep disruption.

In some embodiments, a positive airway pressure device is disclosed herein. The positive airway pressure device includes a blower, a chamber, a sensor, and a controller. The chamber is downstream of the blower. The chamber is configured to receive gas generated by the blower and output the gas to a patient. The sensor is at least partially disposed in a gas pathway. The sensor is configured to measure a pressure in the chamber. The controller is in communication with the blower and the sensor. The controller is configured to perform operations. The operations include initializing the blower to deliver a therapy pressure to the patient. The operations further include receiving, from the sensor, real-time respiratory response data while delivering therapy to the patient. The operations further include generating, via a machine learning model, a predicted respiratory response based on the real-time respiratory response data and the therapy pressure delivered to the patient. The operations further include comparing the predicted respiratory response to the real-time respiratory response data. The operations further include, based on the comparing, determining that a sleep disruption has occurred based on a threshold deviation between the predicted respiratory response and the real-time respiratory response data. The operations further include, based on the determining, initiating an action to account for the sleep disruption.

In some embodiments, a method for detecting a sleep disruption using a positive airway pressure device is disclosed herein. A controller of the positive airway pressure device determines a baseline respiratory response for a patient by collecting, via a sensor at least partially disposed in a gas pathway, respiratory response data from the patient for a plurality of pressure levels. The controller initializes a blower of the positive airway pressure device to deliver a therapy pressure to the patient. The controller receives, from the sensor, real-time respiratory response data while delivering therapy to the patient. The controller analyzes the real-time respiratory response data to determine whether a sleep disruption has occurred by comparing the real-time respiratory response data to the baseline respiratory response for the patient. Based on the analyzing, the controller determines that a sleep disruption has occurred based on an anomaly detected in the real-time respiratory response data. Based on the determining, the controller initiates an action to account for the sleep disruption.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrated only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Non-invasive Positive Air Pressure devices (PAPs) are used for treating a number of respiratory disorders including Obstructive sleep apnea-hypopnea syndrome (OSAHS) and Obstruction Sleep Apnea, OSA. These disorders are characterized by repetitive episodes of airflow reduction (hypopnea) or cessation (apnea), which events may broadly be described as "sleep disruptions."

In many cases it is useful to understand the patient's respiratory response to therapy being administered from the PAP device. In treating sleep disruptions, the respiratory response is often used to influence the therapy by increasing or decreasing the therapy pressure within prescribed limits of the administering physician. In some conventional PAP devices the pressure is preset and remains the same during therapy. Even in these applications, however, the patient may experience discomfort exhaling under the therapy pressure. In such scenarios, the therapy pressure may be lowered during the initial phase of expiration to allow the patient to exhale more comfortably.

In other clinical applications for the PAP device, the pressure may be changed during therapy to provide one set pressure during inspiration and another set pressure during expiration. These devices are bi-level and the pressures are typically determined by the prescribing clinician.

In other clinical applications, PAP devices may also operate in a viable mode, also known as Auto CPAP. In viable mode, the initial therapy may be prescribed by a clinician. As the patient breaths, the respiratory response is analyzed to determine if a sleep disruption occurs. The frequency of the sleep disruptions may be referred to as the AHI (Apnea/Hypopnea Index) and is indicated in events/hour. The sleep disruptions may be characterized by the shape of the patient's respiratory response. For example, breathing response may be uneven resulting in lapses between breaths or very uneven, resulting in snoring or other conditions.

One or more techniques described herein provide an improved way to detect sleep disruptions during therapy. In some embodiments, one or more techniques described herein provide an algorithmic approach to detecting sleep disruptions, based on obtaining and learning a patient's baseline respiratory response data. Based on the baseline respiratory response data, the system may be able to detect deviations from the baselines, which may be attributed to a sleep disruption. In some embodiments, one or more techniques described herein provide an artificial intelligence based approach to detecting sleep disruptions. For example, a training module may train an artificial intelligence algorithm to project what should be the patient's respiratory response based on various inputs. If the measured respiratory response deviates from the expected respiratory response, such deviation may be attributed to a sleep disruption.

Figure 1:
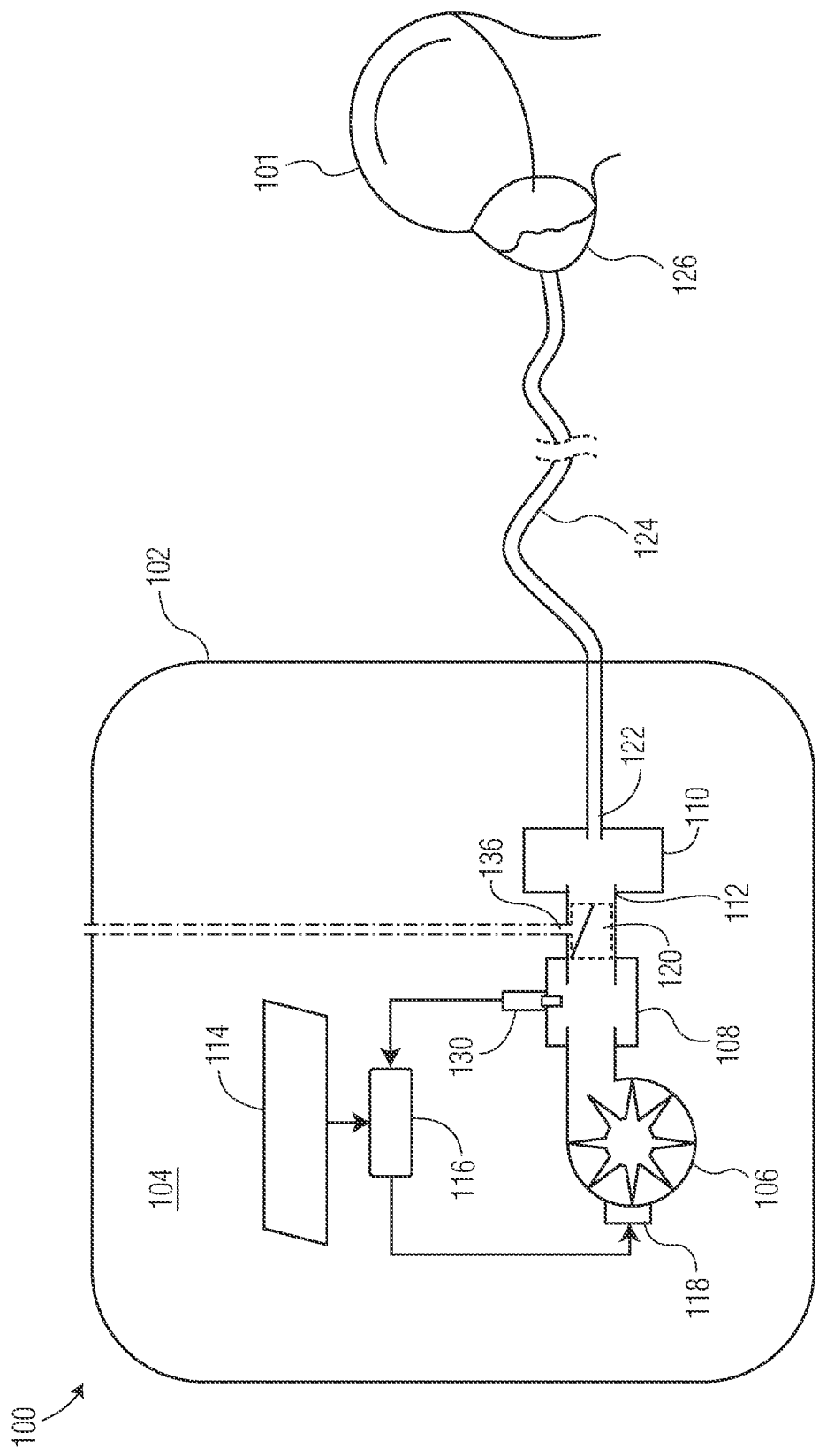
FIG. 1 is a block diagram illustrating a positive airway pressure (PAP) device with interface to a patient, according to example embodiments.

FIG. 1 is a block diagram illustrating a positive airway pressure (PAP) device 100 with interface to a patient 101, according to example embodiments. As shown, PAP device 100 may include a body 102 defining an interior volume 104. PAP device 100 may include a blower 106, a gas manifold 108, a buffer chamber 110, a connector 112, and a microprocessor 114 disposed in interior volume 104.

Blower 106 may be configured to deliver air to gas manifold 108. Blower 106 may include a blower controller 116 associated therewith. Blower controller 116 may be configured to control operation of blower 106. For example, blower controller 116 may be configured to provide electrical input to blower 106 to control a speed of blower 106. For example, blower controller 116 may provide blower 106 with electrical input to obtain a setpoint pressure. In some embodiments, blower controller 116 may provide electrical input to blower terminal block 118 to control speed of blower 106. The speed of blower 106 may be directly related to the maintained pressure.

Gas manifold 108 may be configured to fluidly couple blower 106 with buffer chamber 110. Buffer chamber 110 may be configured to maintain a volume of gas that is removed from blower 106. For example, gas may flow from blower 106, through gas manifold 108, and into buffer chamber 110.

Connector 112 may be configured to couple buffer chamber 110 with gas manifold 108. Connector 112 may provide a flow channel from gas manifold 108 to buffer chamber 110. As shown, in some embodiments, connector 112 may include check valve 120. Check valve 120 may be representative of a one-way valve or gate configured to prevent backflow of gas into blower 106. For example, check valve 120 may be configured to prevent gas at higher pressure from flowing back into blower 106 from buffer chamber 110. If, for example, blower 106 is turned off, check valve 120 may be configured to prevent air from escaping back through blower 106. Such prevention may result in a more consistent control of the delivered pressure and may reduce influence from a patient's respiratory response. In some embodiments, check valve 120 may be designed such that, when blower 106 is turned off, check valve 120 may open a path to external air. For example, check valve 120 may open a path to external air via check valve vent 136, thus allowing for any backflow pressure or gas to be exhausted from PAP device 100. Vent 136 may be located proximate the exterior of PAP device 100. Such functionality may ensure that the patient is not asphyxiated in the case of a power failure.

Although PAP device 100 is illustrated as including a gas manifold 108 and a buffer chamber 110, in some embodiments, PAP device 100 may simply include a single unit acting as both gas manifold 108 and buffer chamber 110.

As shown, PAP device 100 may further include a patient connection port 122. Patient connection port 122 may be configured to output gas to a patient delivery system 124. For example, patient connection port 122 may be representative of a port in communication with buffer chamber 110.

In operation, patient delivery system 124 may be detachably coupled to PAP device 100. Patient delivery system 124 may be representative of tubing that delivers gas to patient 101 via patient interface 126 (e.g., mask).

PAP device 100 may further include a sensor 130. Sensor 130 may be positioned in a gas pathway of PAP device 100. For example, a gas pathway may refer to the flow channel encompassing all areas where the air flows from the air intake through to patient connection port 122. In some embodiments, such as that shown, sensor 130 may be at least partially disposed in gas manifold 108. In some embodiments, sensor 130 may be at least partially disposed in blower 106. Generally, sensor 130 may be disposed anywhere within PAP device 100 such that it is in close proximity to blower 106. Sensor 130 may be configured to monitor pressure and provide feedback to blower controller 116 such that blower controller 116 can maintain a set pressure. For example, sensor 130 may send to blower controller 116 a control signal that represents a measured pressured in gas manifold 108. If the setpoint pressure differs from the control signal pressure, blower controller 116 may increase or decrease the speed of blower 106 to maintain the setpoint pressure. In this manner, blower controller 116 may work in conjunction with sensor 130 to provide a feedback loop for maintaining a desired level of pressure.

Although not explicitly shown, those skilled in the art understand that more than one sensor may be implemented in the following processes. For example, U.S. application Ser. No. 17/659,971, which is incorporated by reference herein in its entirety, describes a two sensor PAP device that may implement the present processes. In such embodiments, a first sensor may be used for training while the second sensor may be used for control.

Microprocessor 114 may be configured to control operation of PAP device 100. For example, microprocessor 114 may be configured to control the pressure setpoint of blower 106. In some embodiments, the initial set point of blower 106 may be referred to as the therapy pressure. The therapy pressure may be set by the user or automatically determined by microprocessor 114. The therapy pressure may be delivered to patient 101 when patient 101 inspires. In some embodiments, the pressure delivered to patient 101 may be adjusted, based on various triggers.

Microprocessor 114 may be configured to monitor patient respiratory response data, based on feedback from sensor 130, to detect a sleep disruption. Based on the detected sleep disruption, microprocessor 114 may be able to dynamically adjust the pressure provided to patient 101 during operation of PAP device 100. For example, microprocessor 114 may adjust the pressure delivered to patient 101 by sending a control signal to blower controller 116 to set blower controller 116 to a different pressure level.

In some embodiments, microprocessor 114 may be configured to algorithmically identify a sleep disorder by learning a baseline respiratory pattern of patient 101 and comparing consecutive respiratory cycles of patient 101 to the baseline respiratory pattern.

In some embodiments, microprocessor 114 may determine that patient 101 has experienced a sleep disorder based on a change in frequencies of respiration. For example, generally, a change in frequency that is longer than a baselines frequency for a normal respiratory cycle typically is typically caused by a sleep disorder.

In some embodiments, microprocessor 114 may determine that patient 101 has experienced a sleep disorder based on a comparison of amplitudes between consecutive respiratory cycles. For example, microprocessor 114 may determine that smaller or larger than baseline amplitudes may be an indication of a sleep disruption. In another example, microprocessor 114 may determine that erratic amplitudes (e.g., frequent alternating between a higher or lower amplitude compared to baseline) may be an indication of a sleep disorder.

In some embodiments, microprocessor 114 may determine that patient 101 has experienced a sleep disorder based on a shape of the respiratory response curve. For example, small spikes in the respiratory response curve may signal a sleep disruption. In another example, the respiratory response curve leading or lagging behind a baseline respiratory response curve may signal a sleep disruption.

In some embodiments, microprocessor 114 may utilize one or more artificial intelligence techniques to determine sleep disruptions. For example, microprocessor 114 may include a trained machine learning model which may be configured to predict a respiratory response curve of patient 101 based on one or more input variables. Microprocessor 114 may classify a respiratory response that differs from a predicted respiratory response as an anomaly. In some embodiments, microprocessor 114 may assign a confidence score to the abnormality indicating a degree or level of confidence that the deviation differs. If, for example, the confidence score is greater than a predetermined value, then the abnormality may be considered significant and classified as a sleep disruption.

In some embodiments, the machine learning model may further be trained to identify a cause of the sleep disruption. For example, the machine learning model may be trained to identify the cause or type of apnea experienced by patient 101. For example, a clinician may be able to provide labeled training data to the machine learning model. The labeled training data may include the clinician analyzing respiratory response curves, tagging abnormal patters, and labeling the type of abnormality present (e.g., snoring, hypopnea, apneayes, etc.).

Once a sleep disruption is identified, microprocessor 114 may take an action. In some embodiments, the action may be in the form of an alert to a clinician. In some embodiments, the action may be to adjust the pressure of PAP device 100 by sending a control signal to blower controller 116.

Although blower controller 116 and microprocessor 114 are shown as separate components, those skilled in the art understand that blower controller 116 and microprocessor 114 can be a single computing device.

Figure 2:
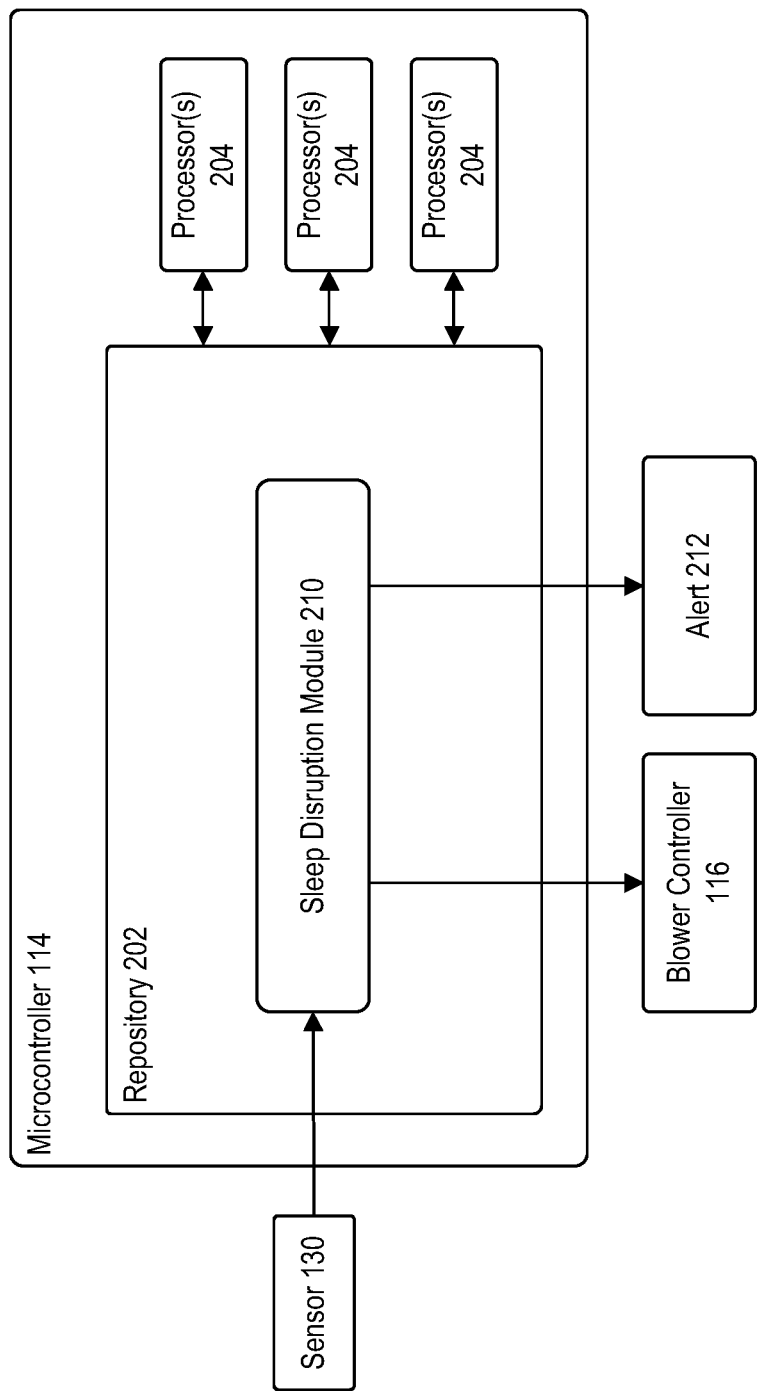
FIG. 2 is a block diagram illustrating microprocessor, according to example embodiments.

FIG. 2 is a block diagram 200 illustrating microprocessor 114, according to example embodiments. As shown, microprocessor 114 includes repository 202 and one or more computer processors 204.

Repository 202 may be representative of any type of storage unit and/or device (e.g., a file system, database, collection of tables, or any other storage mechanism) for storing data. Further, repository 202 may include multiple different storage units and/or devices. The multiple different storage units and/or devices may or may not be of the same type or located at the same physical site. As shown, repository 202 includes at least sleep disruption module 210.

Sleep disruption module 210 may be comprised of one or more software modules. The one or more software modules are collections of code or instructions stored on a media (e.g., memory of microprocessor 114) that represent a series of machine instructions (e.g., program code) that implements one or more algorithmic steps. Such machine instructions may be the actual computer code the processor of microprocessor 114 interprets to implement the instructions or, alternatively, may be a higher level of coding of the instructions that are interpreted to obtain the actual computer code. The one or more software modules may also include one or more hardware components. One or more aspects of an example algorithm may be performed by the hardware components (e.g., circuitry) itself, rather than as a result of the instructions.

Sleep disruption module 210 may be configured to learn a patient's respiratory response patterns in order to identify a sleep disruption. To identify a sleep disruption, sleep disruption module 210 may undergo a training process, in which sleep disruption module 210 learns a baseline respiratory response of patient 101.

Sleep disruption module 210 may receive pressure recordings from sensor 130. For example, sensor 130 may be configured to record patient's 101 respiratory response at one or more therapy pressures. In some embodiments, sensor 130 may be configured to record patient's 101 respiratory response at a minimum of two pressures. For example, sensor 130 may be configured to record patient's 101 respiratory response at a plurality of pressure levels between a minimum pressure and a maximum pressure, as prescribed by the clinician. Using a more specific example, if the clinician prescribes pressures between 4 cm $H_2O$ and 10 cm $H_2O$, then the number of pressures selected for training may include at least 4 cm $H_2O$ and 10 cm $H_2O$, and also multiple pressures between 4 cm $H_2O$ and 10 cm $H_2O$, such as, but not limited to, 6 cm $H_2O$ and 8 cm $H_2O$.

To facilitate this process, microprocessor 114 may send control signals to blower controller 116 that cause blower controller 116 to adjust the speed of blower 106, which, in turn, affects the pressure provided to patient 101.

In some embodiments, sleep disruption module 210 may gather patient's 101 respiratory response data for a set period of time. For example, sleep disruption module 210 may collect sensor data from sensor 130 for a minimum of about one minute at each pressure level. In some embodiments, sleep disruption module 210 may gather patient's 101 respiratory response data for a set number of respiratory cycles. For example, sleep disruption module 210 may collect sensor data from sensor 130 for a minimum of 5 cycles.

In some embodiments, sleep disruption module 210 may gather patient's 101 respiratory response data during a normal sleep period. For example, during a sleep period, microprocessor 114 may program PAP device 100 to adjust the pressure between the minimum and maximum pressures as prescribed by the clinician. Patient 101 can deploy PAP device 100 and can proceed to sleep as normal.

In some embodiments, sleep disruption module 210 may gather patient's 101 respiratory response data while patient 101 is awake. For example, during a pre-sleep cycle, microprocessor 114 may program PAP device 100 to adjust the pressure between the minimum and maximum pressures as prescribed by the clinician. In some embodiments, to ensure that the respiratory response data is accurate, data collection by sensor 130 may begin several minutes after therapy is begun. This may be to ensure patient 101 is calm and relaxed before collection of data.

Based on the respiratory response data collected by sensor 130, sleep disruption module 210 may identify or learn a baseline respiratory response of patient 101 for identifying sleep disruptions. Sleep disruption module 210 may include one or more algorithms to be applied during therapy. For example, sleep disruption module 210 may utilize a rate of respiration algorithm. An exemplary respiration algorithm may be: if the instantaneous respiration rate ($RR_i$) is greater than the baseline respiration rate ($RR_n$), then sleep disruption module 210 may cause blower controller 116 to increase the speed of blower 106, such that the pressure delivered to patient 101 is increased by about 0.5 cm H2O. The instantaneous respiration rate ($RR_i$) being greater than the baseline respiration rate ($RR_n$) may signal a sleep disruption.

In some embodiments, sleep disruption module 210 may analyze the waveform harmonics of the patient's 101 respiratory cycle for identifying sleep disruptions. For example, sleep disruption module 210 may compare the instantaneous harmonic from sensor data to the baseline harmonic. In some embodiments, sleep disruption module 210 may use at least the fundamental harmonic. In some embodiments, sleep disruption module 210 may use the fundamental harmonic, the second harmonic, the third harmonic, and/or higher level harmonics for determining a sleep disruption. If the instantaneous harmonic differs from the baseline harmonic by a threshold amount, then sleep disruption module 210 may conclude that a sleep disruption has occurred.

In some embodiments, responsive to detecting a sleep disruption, sleep disruption module 210 may send a control signal to blower controller 116. The control signal may prompt blower controller 116 to adjust the speed of blower 106, which, in turn, affects the pressure delivered to patient 101.

In some embodiments, responsive to detecting a sleep disruption, sleep disruption module 210 may issue an alert 212. For example, sleep disruption module 210 may issue an alert over one or more networks to a clinician computing device to alert the clinician of patient 101 of the sleep disruption.

Figure 3:
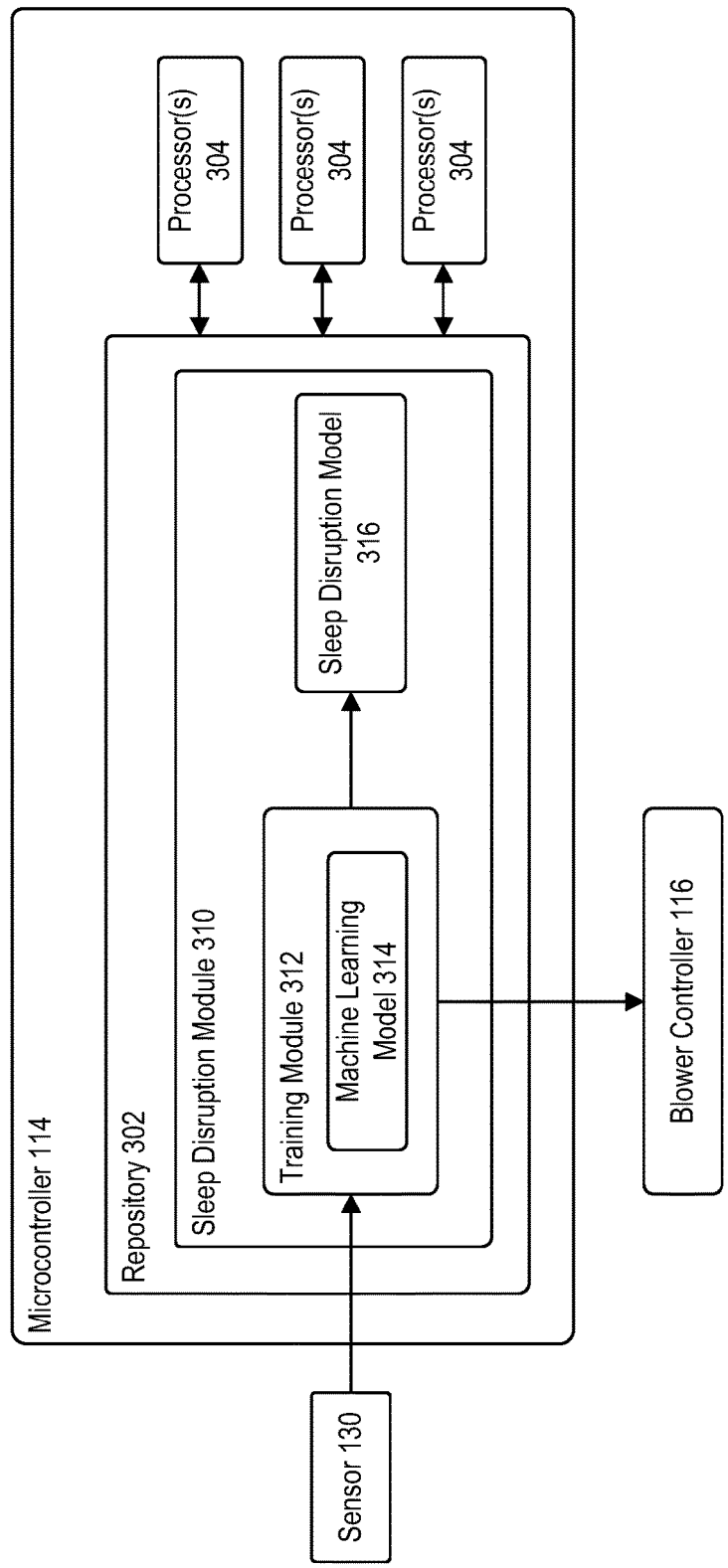
FIG. 3 is a block diagram illustrating microprocessor, according to example embodiments.

FIG. 3 is a block diagram 300 illustrating microprocessor 114, according to example embodiments. As shown, microprocessor 114 includes repository 302 and one or more computer processors 304.

Repository 302 may be representative of any type of storage unit and/or device (e.g., a file system, database, collection of tables, or any other storage mechanism) for storing data. Further, repository 302 may include multiple different storage units and/or devices. The multiple different storage units and/or devices may or may not be of the same type or located at the same physical site. As shown, repository 302 includes at least sleep disruption module 310.

Sleep disruption module 310 may be similar to sleep disruption module 210. For example, sleep disruption module 310 may be configured to learn a patient's respiratory response patterns and detect a sleep disruption based on the learned respiratory response patterns. However, rather than use an algorithmic approach, sleep disruption module 310 may use a deep learning approach to detecting sleep disruptions.

Sleep disruption module 310 may include at least training module 312. Training module 312 may be comprised of one or more software modules. The one or more software modules are collections of code or instructions stored on a media (e.g., memory of microprocessor 114) that represent a series of machine instructions (e.g., program code) that implements one or more algorithmic steps. Such machine instructions may be the actual computer code the processor of microprocessor 114 interprets to implement the instructions or, alternatively, may be a higher level of coding of the instructions that are interpreted to obtain the actual computer code. The one or more software modules may also include one or more hardware components. One or more aspects of an example algorithm may be performed by the hardware components (e.g., circuitry) itself, rather than as a result of the instructions.

Training module 312 may be configured to train machine learning model 314 to learn to detect a sleep disruption. In some embodiments, machine learning model 314 may be representative of one or more machine learning models. Exemplary machine learning models or algorithms may include, but are not limited to, random forest model, support vector machines, neural networks, deep learning models, Bayesian algorithms, Temporal Convolutional Networks, and the like.

For training, training module 312 may train machine learning model 314 to model or project a patient's respiratory response based on one or more inputs. Exemplary inputs may include the therapy pressure, the measured pressure from sensor 130, and the time. In other words, for each time, t, training module 312 may train machine learning model 314 to model or project a patient's respiratory response based on the therapy pressure at a time t and the measured pressure from sensor 130 at the time t.

Training module 312 may collect training data in a similar manner to that described above in conjunction with FIG. 2. Training module 312 may receive measured pressure recordings from sensor 130. For example, sensor 130 may be configured to record patient's 101 respiratory response at one or more therapy pressures. In some embodiments, sensor 130 may be configured to record patient's 101 respiratory response at a minimum of two pressures. For example, sensor 130 may be configured to record patient's 101 respiratory response at a plurality of pressure levels between a minimum pressure and a maximum pressure, as prescribed by the clinician. Using a more specific example, if the clinician prescribes pressures between 4 cm H2O and 10 cm H2O, then the number of pressures selected for training may include at least 4 cm H2O and 10 cm H2O, and also multiple pressures between 4 cm H2O and 10 cm H2O, such as, but not limited to, 6 cm H2O and 8 cm H2O.

To facilitate this process, microprocessor 114 may send control signals to blower controller 116 that cause blower controller 116 to adjust the speed of blower 106, which, in turn, affects the pressure provided to patient 101.

In some embodiments, training module 312 may gather patient's 101 respiratory response data for a set period of time. For example, training module 312 may collect sensor data from sensor 130 for a minimum of about one minute at each pressure level. In some embodiments, training module 312 may gather patient's 101 respiratory response data for a set number of respiratory cycles. For example, training module 312 may collect sensor data from sensor 130 for a minimum of 5 cycles.

In some embodiments, training module 312 may gather patient's 101 respiratory response data during a normal sleep period. For example, during a sleep period, microprocessor 114 may program PAP device 100 to adjust the pressure between the minimum and maximum pressures as prescribed by the clinician. Patient 101 can deploy PAP device 100 and can proceed to sleep as normal.

In some embodiments, training module 312 may gather patient's 101 respiratory response data while patient 101 is awake. For example, during a pre-sleep cycle, microprocessor 114 may program PAP device 100 to adjust the pressure between the minimum and maximum pressures as prescribed by the clinician. In some embodiments, to ensure that the respiratory response data is accurate, data collection by sensor 130 may begin several minutes after therapy is begun. This may be to ensure patient 101 is calm and relaxed before collection of data.

Based on the respiratory response data collected by sensor 130, training module 312 may train machine learning model 314 to detect sleep disruptions. The inputs to machine learning model 314 may include, but are not limited to, patient respiratory pressure, time of pressure measurement, and the set or applied pressure (e.g., therapy pressure). In some embodiments, other inputs to machine learning model 314 may include biometric data, such as, but not limited to, heart rate and blood oxygen level.

Following training, a trained sleep disruption model 316 may be deployed for detecting sleep disruptions in real-time or near real-time.

In some embodiments, such training process may be used to switch pressures delivered to patient 101 based upon the timing of the patient's inspiration or expiration. For example, training module 312 may utilize the training data to anticipate the change in respiratory state. By knowing, for example, the normal breathing pattern leading up to the end of inspiration, the timing of the point of expiration may be predicted.

Figure 4:
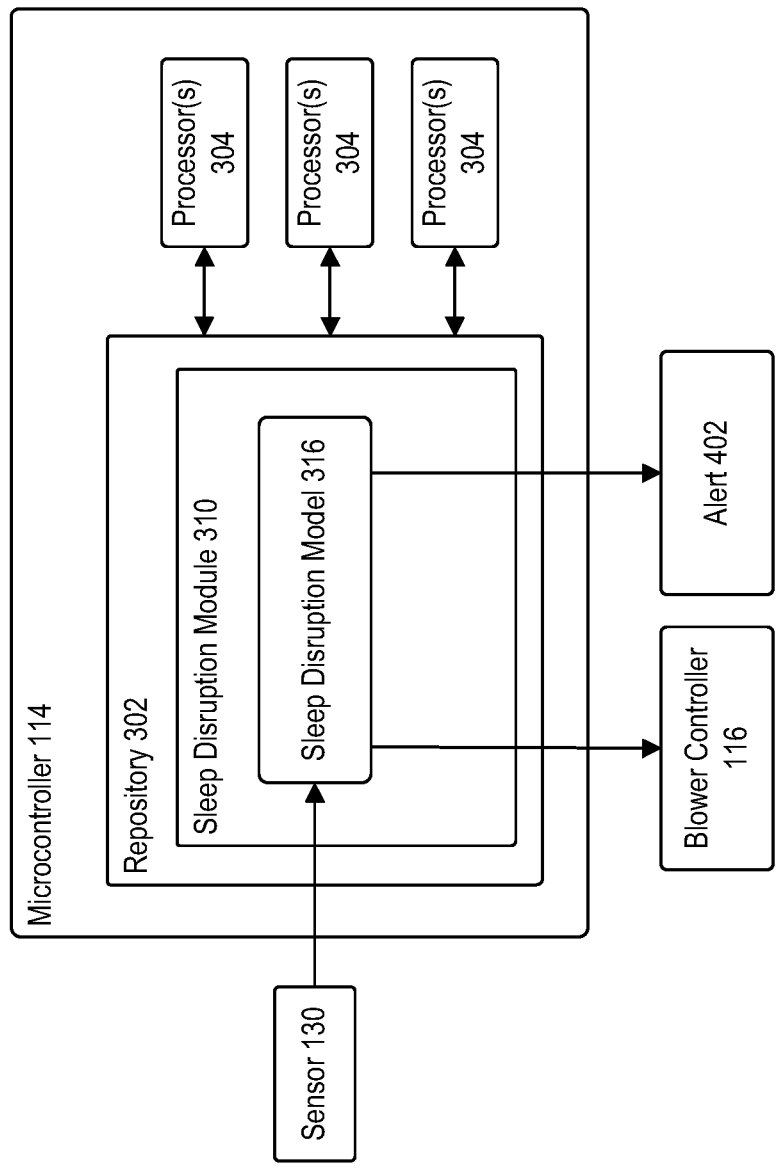
FIG. 4 is a block diagram illustrating microprocessor, according to example embodiments.

FIG. 4 is a block diagram 400 illustrating microprocessor 114, according to example embodiments. As shown, block diagram 400 may illustrate a trained sleep disruption model 316 deployed in sleep disruption module 310.

In operation, sleep disruption model 316 may receive real-time or near real-time respiratory response data from sensor 130. The real-time or near real-time respiratory response data may include, but is not limited to, patient respiratory pressure, time of pressure measurement, and the set or applied pressure (e.g., therapy pressure). In some embodiments, sleep disruption model 316 may further receive real-time or near real-time biometric data, such as, but not limited to, heart rate and blood oxygen level.

Based on the inputs, sleep disruption model 316 may project or predict a respiratory response of patient 101. Sleep disruption model 316 may compare the projected respiratory response to the actual respiratory response of patient 101. A respiratory response which differs from the prediction may be classified as an anomaly. Sleep disruption model 316 may assign a confidence score to the anomaly. For example, sleep disruption model 316 may identify a correlation coefficient in a standard regression model to assign a confidence score to the abnormality. The confidence score may indicate a degree or level of confidence that the deviation differs from the projected respiratory response. If the confidence score is greater than a threshold value, sleep disruption model 316 may classify the anomaly as a sleep disruption.

In some embodiments, responsive to detecting a sleep disruption, sleep disruption model 316 may send a control signal to blower controller 116. The control signal may prompt blower controller 116 to adjust the speed of blower 106, which, in turn, affects the pressure delivered to sleep disruption module 310.

In some embodiments, responsive to detecting a sleep disruption, sleep disruption model 316 may issue an alert 402. For example, sleep disruption model 316 may issue an alert over one or more networks to a clinician computing device to alert the clinician of patient 101 of the sleep disruption.

Figure 5:
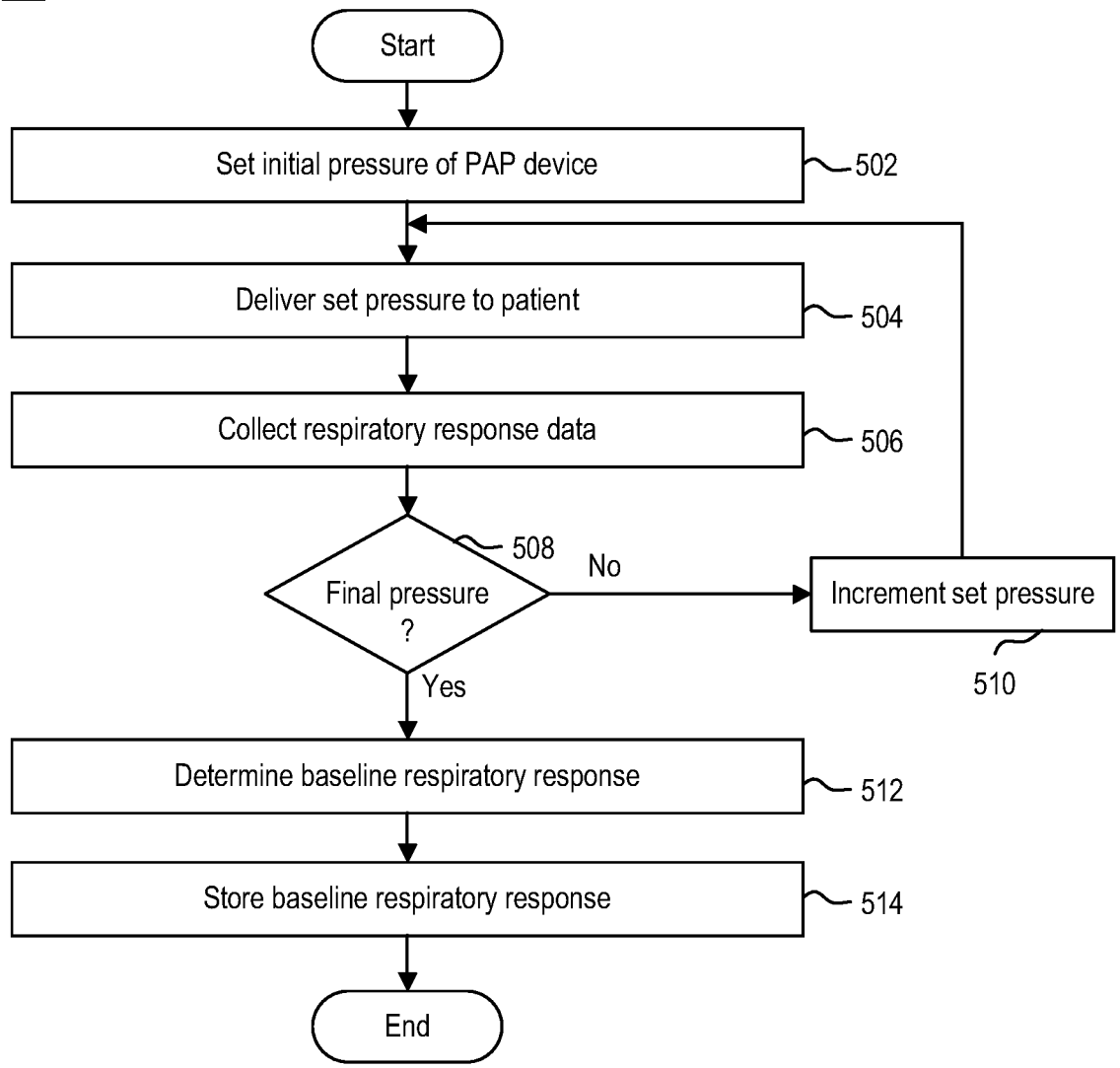
FIG. 5 is flow diagram illustrating a method of establishing a baseline respiratory response for a patient, according to example embodiments.

FIG. 5 is flow diagram illustrating a method 500 of establishing a baseline respiratory response for a patient, according to example embodiments. Method 500 may begin at step 502.

At step 502, microprocessor 114 may set the initial pressure of PAP device 100. For example, microprocessor 114 may send a control signal to blower controller 116 that instructs blower controller 116 to set a speed of blower 106 to achieve the initial pressure delivered to patient 101. In some embodiments, the initial pressure may be representative of the minimum pressure prescribed by a clinician. For example, the initial pressure may be set at 4 cm H2O.

At step 504, PAP device 100 may deliver the set pressure to patient 101. For example, blower 106 may be set at a speed, such that the initial pressure is achieved. PAP device 100 may deliver the set pressure to patient 101 via patient delivery system 124.

At step 506, microprocessor 114 may collect respiratory response data based on the set pressure delivered to patient 101. For example, during delivery of set pressure, sensor 130 may record pressure readings. Sensor 130 may provide those pressure readings to patient 101.

In some embodiments, microprocessor 114 may gather patient's respiratory response data for a set period of time at the set pressure. For example, sleep disruption module 210 may collect sensor data from sensor 130 for a minimum of about one minute at the set pressure. In some embodiments, sleep disruption module 210 may gather patient's 101 respiratory response data for a set number of respiratory cycles. For example, sleep disruption module 210 may collect sensor data from sensor 130 for a minimum of 15 cycles at the set pressure.

At step 508, microprocessor 114 may determine whether a final pressure has been reached. For example, as discussed above, sensor 130 may be configured to record patient's 101 respiratory response at a plurality of therapy pressures. In some embodiments, sensor 130 may be configured to record patient's 101 respiratory response at a minimum of two pressures. For example, sensor 130 may be configured to record patient's 101 respiratory response at a plurality of pressure levels between a minimum pressure and a maximum pressure, as prescribed by the clinician. Using a more specific example, if the clinician prescribes pressures between 4 cm $H_2O$ and 10 cm $H_2O$, then the number of pressures selected for training may include at least 4 cm $H_2O$ and 10 cm $H_2O$, and also multiple pressures between 4 cm $H_2O$ and 10 cm $H_2O$, such as, but not limited to, 6 cm $H_2O$ and 8 cm $H_2O$.

If, at step 508, microprocessor 114 determines that the final pressure has not been met, then method 500 may proceed to step 510. At step 510, microprocessor 114 may increment the pressure delivered to patient 101. For example, microprocessor 114 may send a control signal to blower controller 116 that instructions blower controller 116 to adjust the speed of blower 106, which, in turn, adjusts the pressure delivered to patient 101. The new set pressure may then be delivered to patient 101.

If, however, at step 508, microprocessor 114 determines that the final pressure has been met, then method 500 proceeds to step 512. At step 512, microprocessor 114 may determine the patient's baseline respiratory response data based on the collected sensor data. In some embodiments, determining the patient's baseline respiratory response data may include determining a baselines frequency of respiration, determining a baseline amplitude of respiration, determining the shape of the respiratory response curve, flow rate, and the like.

At step 514, microprocessor 114 may store the baseline respiratory response data for later analysis. For example, once deployed, sleep disruption module 210 may compare real-time or near real-time respiratory response data to the baseline respiratory response data to determine whether a sleep disruption has occurred.

Figure 6:
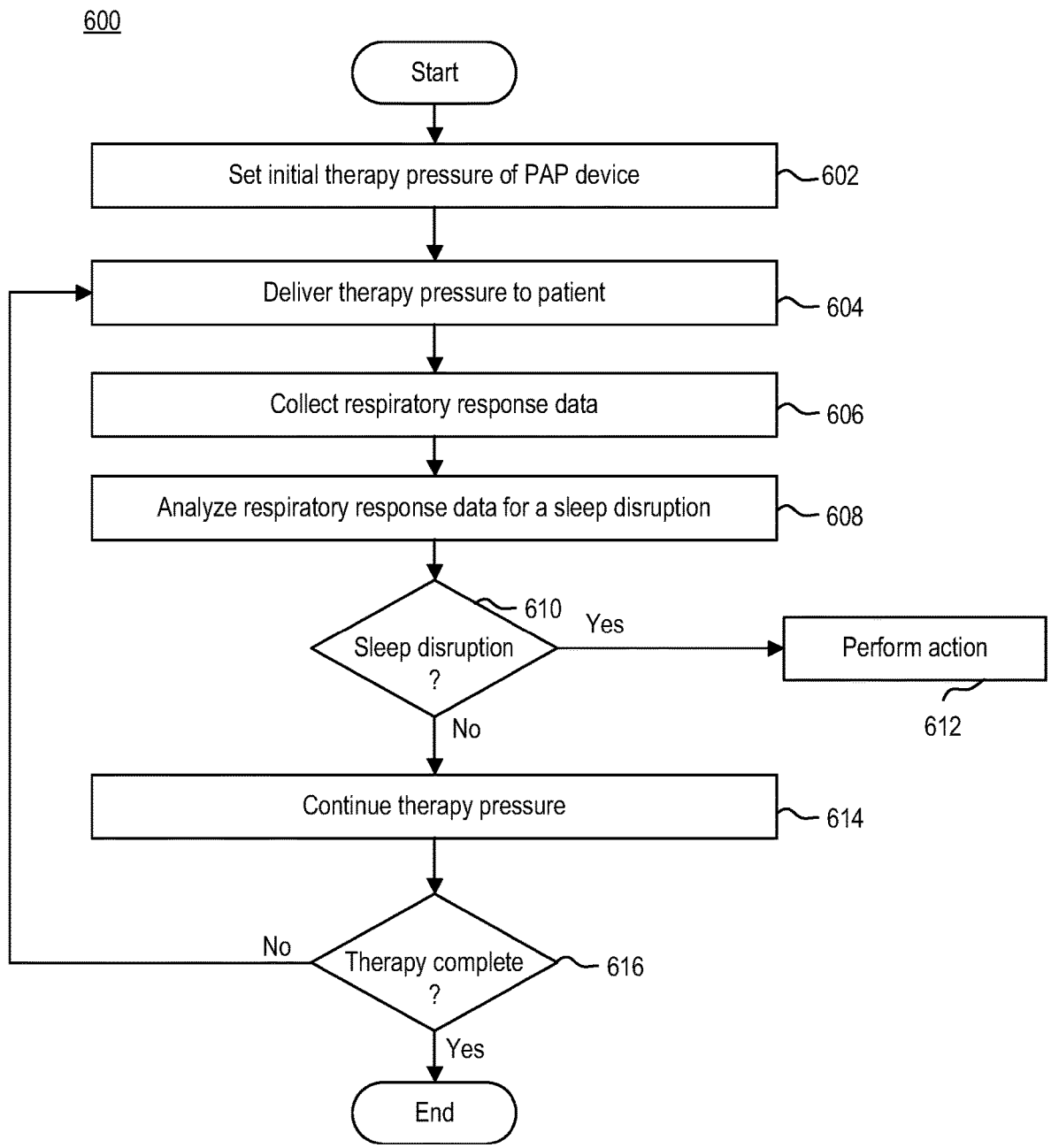
FIG. 6 is a flow diagram illustrating a method of detecting a sleep disruption during PAP therapy, according to example embodiments.

FIG. 6 is a flow diagram illustrating a method 600 of detecting a sleep disruption during PAP therapy, according to example embodiments. Method 600 may begin at step 602.

At step 602, microprocessor 114 may set the initial therapy pressure of PAP device 100. For example, microprocessor 114 may send a control signal to blower controller 116 that instructs blower controller 116 to set a speed of blower 106 to achieve the initial therapy pressure delivered to patient 101.

At step 604, PAP device 100 may deliver the therapy pressure to patient 101. For example, blower 106 may be set at a speed, such that the therapy pressure is achieved. PAP device 100 may deliver the set pressure to patient 101 via patient delivery system 124.

At step 606, microprocessor 114 may collect respiratory response data based on the set pressure delivered to patient 101. For example, during delivery of set pressure, sensor 130 may record pressure readings. Sensor 130 may provide those pressure readings to sleep disruption module 210.

At step 608, microprocessor 114 may analyze the respiratory response to determine whether a sleep disruption has occurred. In some embodiments, analyzing the respiratory response may include sleep disruption module comparing the collected respiratory response data to the patient's baseline respiratory response data determined during the training process. For example, sleep disruption module 210 may compare the received respiratory response data to one or more of the baseline frequency of respiration, the baseline amplitude of respiration, and the baseline shape of the respiratory response curve.

At step 610, microprocessor 114 may determine whether a sleep disruption occurred. If, for example, at step 610, microprocessor 114 determined that a sleep disruption has occurred based on the analysis, then method 600 may proceed to step 612. At step 612, microprocessor 114 may perform some action. In some embodiments, the action may be to send a control signal to blower controller 116 that causes blower controller 116 to change the speed of blower 106, thereby adjusting the therapy pressure delivered to patient 101. In some embodiments, the action may be to issue an alert to a clinician.

If, however, at step 610, microprocessor 114 determines that a sleep disruption did not occur, then method 600 may proceed to step 614. At step 614, microprocessor 114 may continue delivering pressure to patient 101 at the therapy pressure.

At step 616, microprocessor 114 may determine whether the therapy is complete. If, at step 616, microprocessor 114 determines that the therapy is not complete (e.g., patient 101 is still using PAP device 100), then method 600 reverts to step 604. If, however, at step 616, microprocessor 114 determines that the therapy is complete, then method 600 ends.

Figure 7:
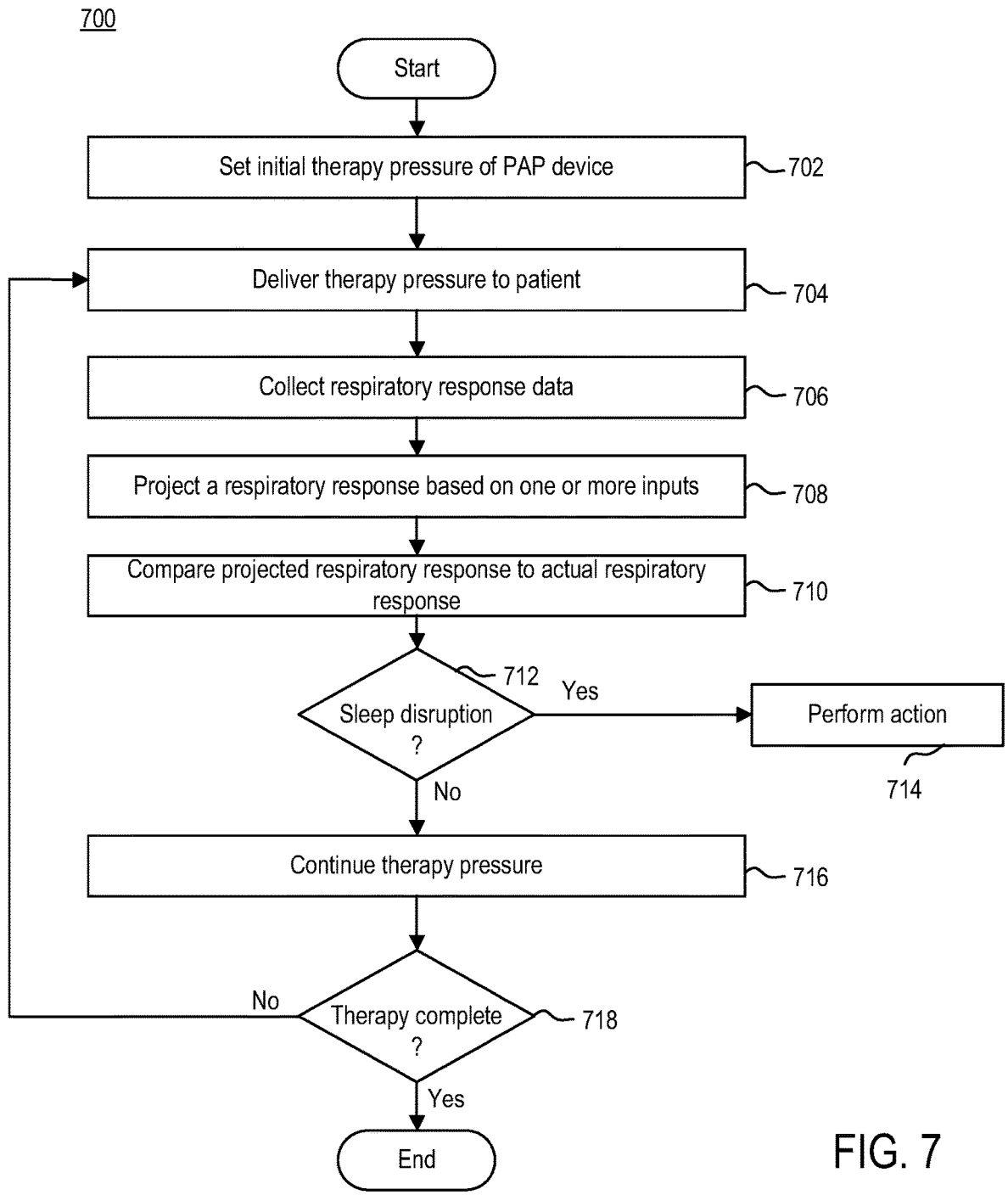
FIG. 7 is a flow diagram illustrating a method of detecting a sleep disruption during PAP therapy, according to example embodiments.

FIG. 7 is a flow diagram illustrating a method 700 of detecting a sleep disruption during PAP therapy, according to example embodiments. Method 700 may begin at step 702.

At step 702, microprocessor 114 may set the initial therapy pressure of PAP device 100. For example, microprocessor 114 may send a control signal to blower controller 116 that instructs blower controller 116 to set a speed of blower 106 to achieve the initial therapy pressure delivered to patient 101.

At step 704, PAP device 100 may deliver the therapy pressure to patient 101. For example, blower 106 may be set at a speed, such that the therapy pressure is achieved. PAP device 100 may deliver the set pressure to patient 101 via patient delivery system 124.

At step 706, microprocessor 114 may collect respiratory response data based on the set pressure delivered to patient

101. For example, during delivery of set pressure, sensor 130 may record pressure readings. Sensor 130 may provide those pressure readings to sleep disruption module 310.

At step 708, microprocessor 114 may project an expected respiratory response based on one or more inputs. For example, sleep disruption module 310 may use trained sleep disruption model 316 to predict a patient's respiratory response based on input data. Exemplary input data may include, but is not limited to, the therapy pressure, the measured therapy pressure, and the time.

At step 710, microprocessor 114 may analyze the respiratory response data to determine whether a sleep disruption has occurred. In some embodiments, analyzing the respiratory response may include sleep disruption module 310 comparing the projected respiratory response to the measured or actual respiratory response. For example, sleep disruption module 310 may compare the prediction from sleep disruption model 316 to a respiratory response generated based on the respiratory response data as measured by sensor 130.

At step 712, microprocessor 114 may determine whether a sleep disruption occurred. If, for example, at step 712, microprocessor 114 determined that a sleep disruption has occurred based on the analysis, then method 700 may proceed to step 714. At step 714, microprocessor 114 may perform some action. In some embodiments, the action may be to send a control signal to blower controller 116 that causes blower controller 116 to change the speed of blower 106, thereby adjusting the therapy pressure delivered to patient 101. In some embodiments, the action may be to issue an alert to a clinician.

In some embodiments, the action to be applied may not be required to be instantaneous or real time. In such embodiments, it is possible to analyze the respiratory response data after the occurrence of one respiratory cycle or more. This may allow microprocessor 114 to compare the actual respiratory response to the response predicted by sleep disruption model 316. For example, at the completion of a respiratory cycle, sleep disruption model 316 may compare the actual respiratory data to the predicted respiratory data. Based on the comparison, sleep disruption model 316 may generate the Root Mean Squared Deviation (RMSD). If, for example, the RMSD is greater than a predetermined value a respiratory abnormality (e.g., sleep disruption) may be defined as having occurred.

If, however, at step 712, microprocessor 114 determines that a sleep disruption did not occur, then method 700 may proceed to step 716. At step 716, microprocessor 114 may continue delivering pressure to patient 101 at the therapy pressure.

At step 718, microprocessor 114 may determine whether the therapy is complete. If, at step 718, microprocessor 114 determines that the therapy is not complete (e.g., patient 101 is still using PAP device 100), then method 700 reverts to step 704. If, however, at step 718, microprocessor 114 determines that the therapy is complete, then method 700 ends.

Figure 8:
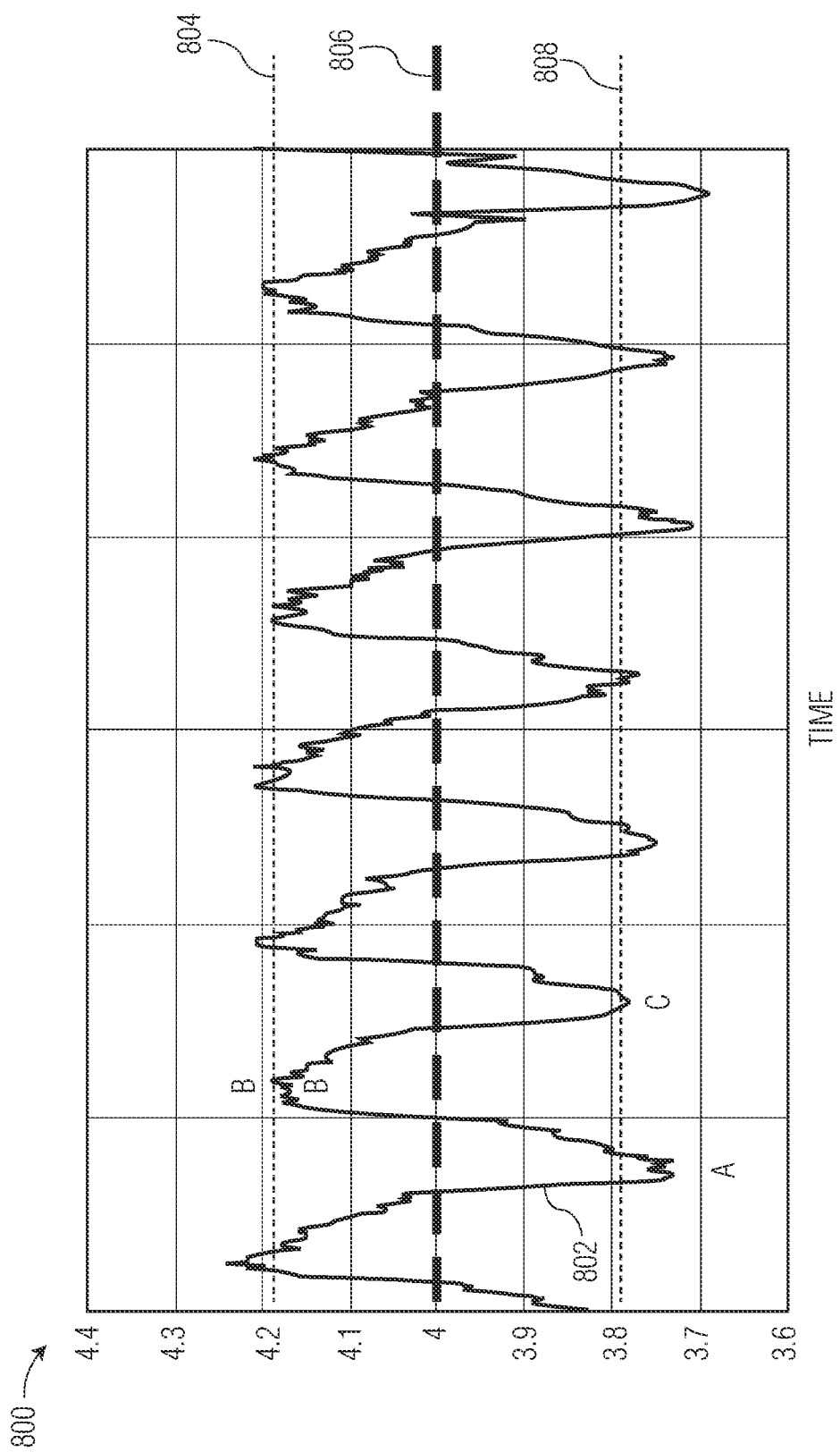
FIG. 8 is a chart illustrating an exemplary respiratory response curve, according to example embodiments.

FIG. 8 is a chart 800 illustrating an exemplary respiratory response curve 802, according to example embodiments. As shown, chart 800 illustrates a respiratory response curve 802, which may be a function of pressure (y-axis) over time (x-axis). Chart 800 includes an upper threshold 804, a lower threshold 808, and a therapy pressure 806. In some embodiments, upper threshold 804 may be a mathematically determined upper threshold. For example, upper threshold 804 may be representative of a pressure that signals the end of expiration and the beginning of inspiration. In some embodiments, upper threshold 804 may be the minimum value of the peaks.

In some embodiments, lower threshold 808 may be a mathematically determined lower threshold. For example, lower threshold 808 may be representative of a pressure that signals the end of inspiration and the beginning of expiration. In some embodiments, lower threshold may be the maximum value of the peaks.

As shown, chart 800 may include several points: A, B, and C. Point A may be representative of the end of inspiration of a first respiratory cycle. Point B may be representative of the end of expiration of the first respiratory cycle. Point C may be representative of the end of inspiration of the second respiratory cycle.

Figure 9:
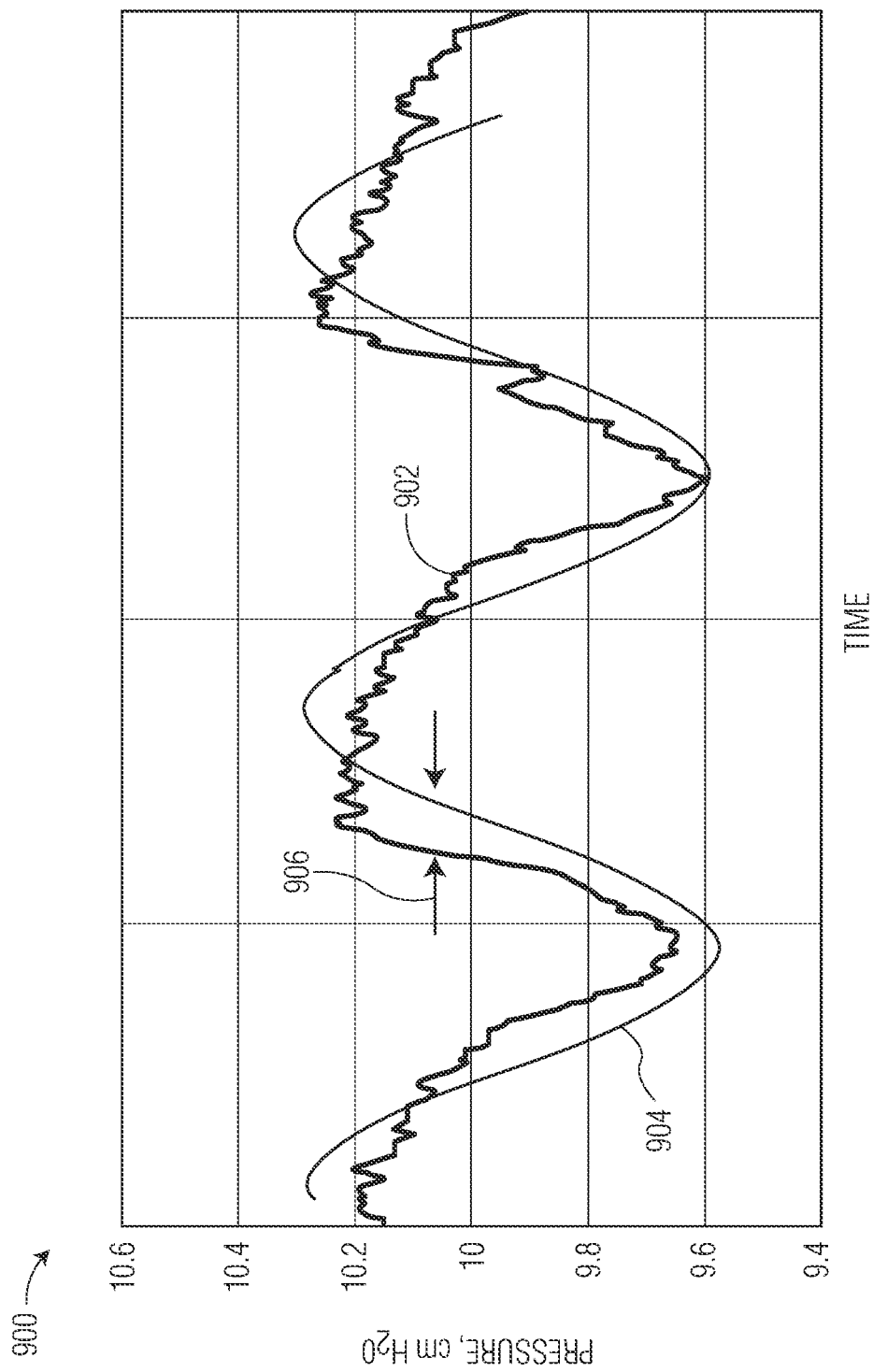
FIG. 9 is a chart illustrating an exemplary respiratory response curve, according to example embodiments.

FIG. 9 is a chart 900 illustrating an exemplary respiratory response curve 902, according to example embodiments. As shown, chart 900 may illustrate an example of a respiratory response curve 902 for a single actual respiratory cycle compared to a predicted respiratory response curve 904, as generated by sleep disruption model 316. As shown, there may be a deviation 906 between the actual respiratory response curve 902 and the predicted respiratory response curve 904. As discussed above, such deviation 906 may signal a sleep disruption.

Figure 10:
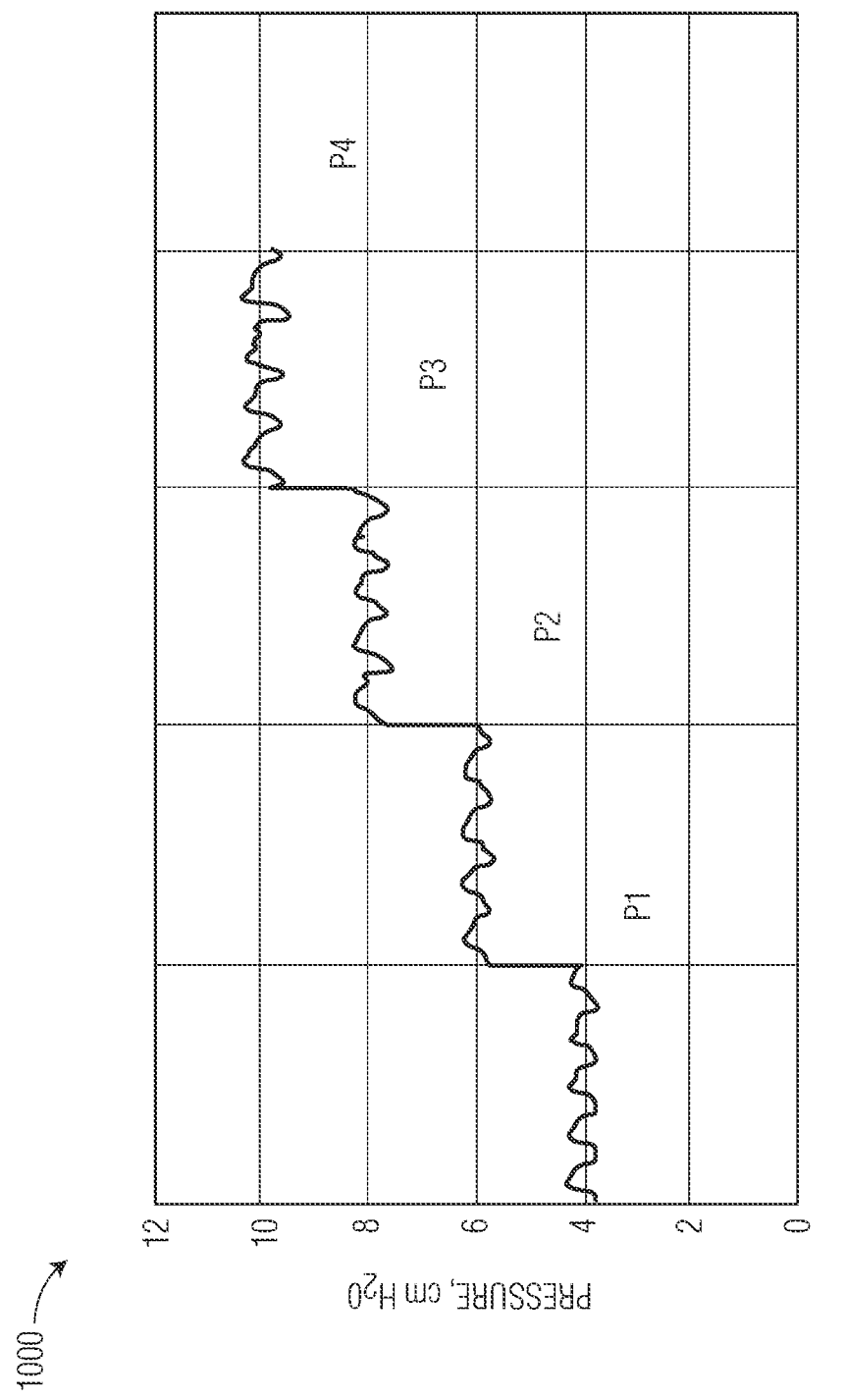
FIG. 10 illustrates an exemplary respiratory graph, according to example embodiments.

FIG. 10 illustrates an exemplary respiratory graph 1000, according to example embodiments. As shown, respiratory graph 1000 may illustrate the changes in therapy pressure delivered to patient 101 during the training process. Sleep disruption module 210 or sleep disruption module 310 may be configured to ramp up the therapy pressure to the user. For example, a first therapy pressure, P1, may be delivered to patient 101 during a first interval of time; a second therapy pressure, P2, may be delivered to patient 101 over a second interval of time; a third therapy pressure, P3, may be delivered to patient 101 over a third interval of time; and a fourth therapy pressure, P4, may be delivered to patient 101 over a fourth period of time. During each interval, sleep disruption module 210 or sleep disruption module 310 may be configured to receive respiratory response data at a respective pressure level from sensor 130. In this manner, sleep disruption module 210 or sleep disruption module 310 may establish a baseline respiratory response for patient 101.

Figure 11:
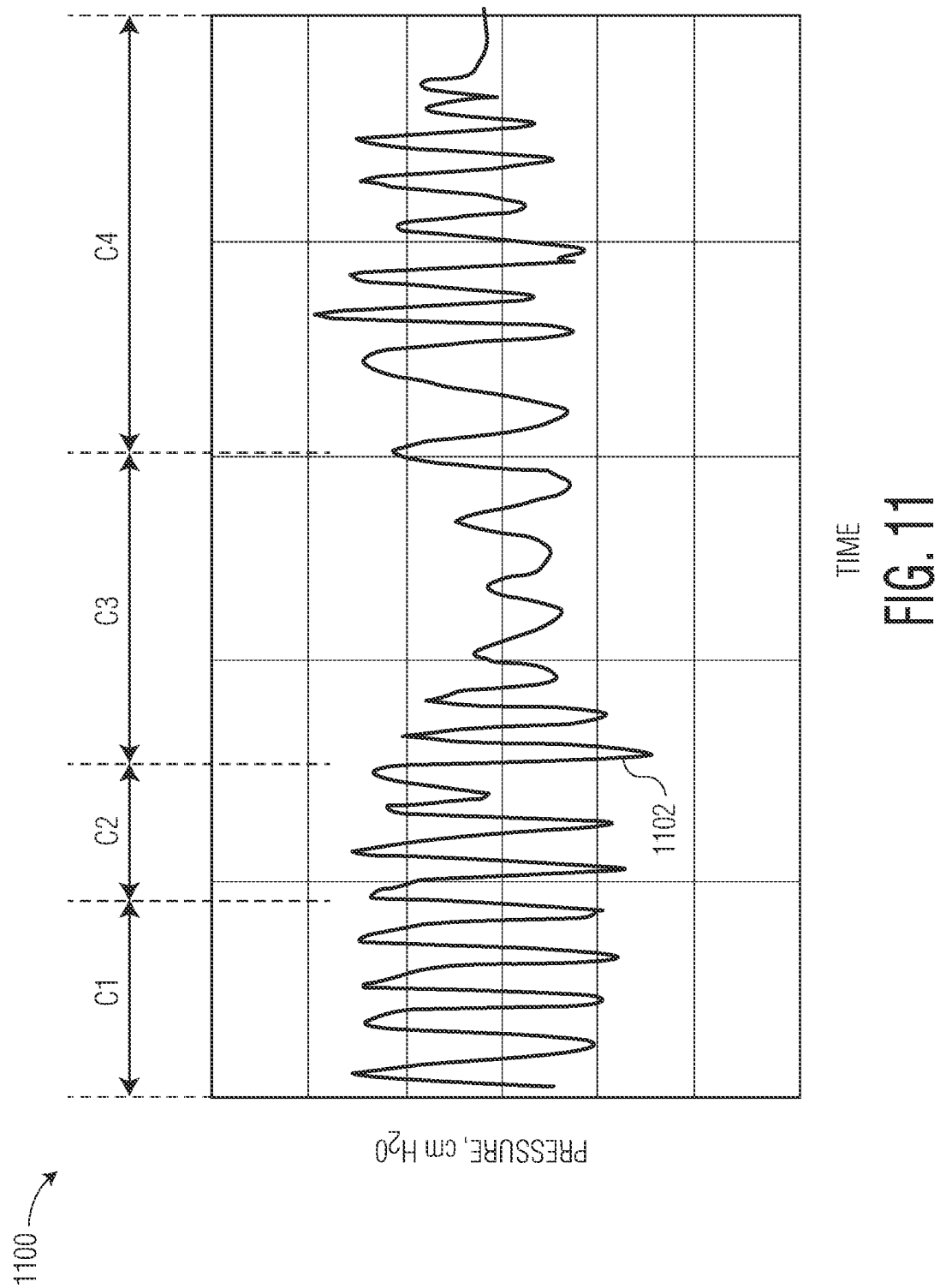
FIG. 11 is a chart illustrating an example respiratory response curve, according to example embodiments.

FIG. 11 is a chart 1100 illustrating an example respiratory response curve 1102, according to example embodiments. As shown, respiratory response curve 1102 may illustrate one or more respiratory abnormalities. For example, respiratory response curve 1102 may include portion C1, portion C2, portion C3, and portion C4. Portion C1 may reflect a normal respiration cycle of a patient. Portion C2 may reflect an erratic, shallow respiratory cycle. Portion C3 may reflect a delayed respiratory cycle. Portion C4 may reflect an erratic respiratory cycle.

Figure 12A:
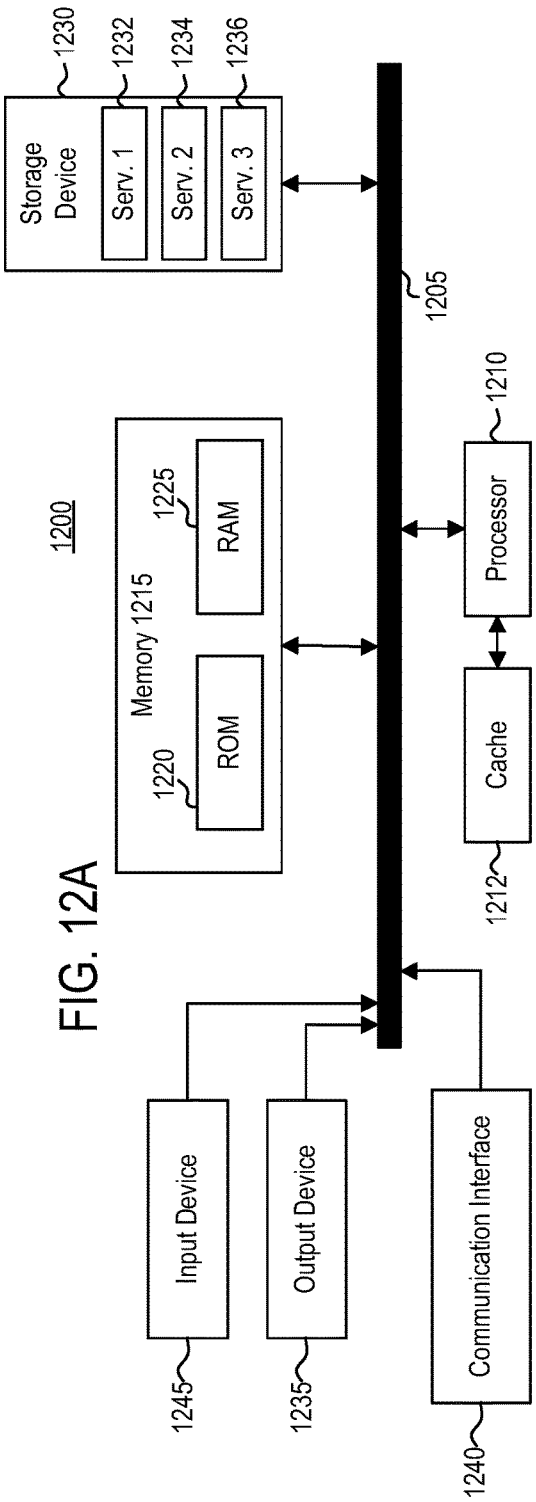
FIG. 12A is a block diagram illustrating a computing device, according to example embodiments.

FIG. 12A illustrates a system bus architecture of computing system 1200, according to example embodiments. System 1200 may be representative of at least a portion of microprocessor 114 and/or blower controller 116. One or more components of system 1200 may be in electrical communication with each other using a bus 1205. System 1200 may include a processing unit (CPU or processor) 1210 and a system bus 1205 that couples various system components including the system memory 1215, such as read only memory (ROM) 1220 and random access memory (RAM) 1225, to processor 1210. System 1200 may include a cache of high-speed memory connected directly with, in close proximity to, or integrated as part of processor 1210.

System 1200 may copy data from memory 1215 and/or storage device 1230 to cache 1212 for quick access by processor 1210. In this way, cache 1212 may provide a performance boost that avoids processor 1210 delays while waiting for data. These and other modules may control or be configured to control processor 1210 to perform various actions. Other system memory 1215 may be available for use as well. Memory 1215 may include multiple different types of memory with different performance characteristics. Processor 1210 may include any general purpose processor and a hardware module or software module, such as service 1 1232, service 2 1234, and service 3 1236 stored in storage device 1230, configured to control processor 1210 as well as a special-purpose processor where software instructions are incorporated into the actual processor design. Processor 1210 may essentially be a completely self-contained computing system, containing multiple cores or processors, a bus, memory controller, cache, etc. A multi-core processor may be symmetric or asymmetric.

To enable user interaction with the computing system 1200, an input device 1245 may represent any number of input mechanisms, such as a microphone for speech, a touch-sensitive screen for gesture or graphical input, keyboard, mouse, motion input, speech and so forth. An output device 1235 may also be one or more of a number of output mechanisms known to those of skill in the art. In some instances, multimodal systems may enable a user to provide multiple types of input to communicate with computing system 1200. Communications interface 1240 may generally govern and manage the user input and system output. There is no restriction on operating on any particular hardware arrangement and therefore the basic features here may easily be substituted for improved hardware or firmware arrangements as they are developed.

Storage device 1230 may be a non-volatile memory and may be a hard disk or other types of computer readable media which may store data that are accessible by a computer, such as magnetic cassettes, flash memory cards, solid state memory devices, digital versatile disks, cartridges, random access memories (RAMs) 1225, read only memory (ROM) 1220, and hybrids thereof.

Storage device 1230 may include services 1232, 1234, and 1236 for controlling the processor 1210. Other hardware or software modules are contemplated. Storage device 1230 may be connected to system bus 1205. In one aspect, a hardware module that performs a particular function may include the software component stored in a computer-readable medium in connection with the necessary hardware components, such as processor 1210, bus 1205, output device 1235 (e.g., display), and so forth, to carry out the function.

Figure 12B:
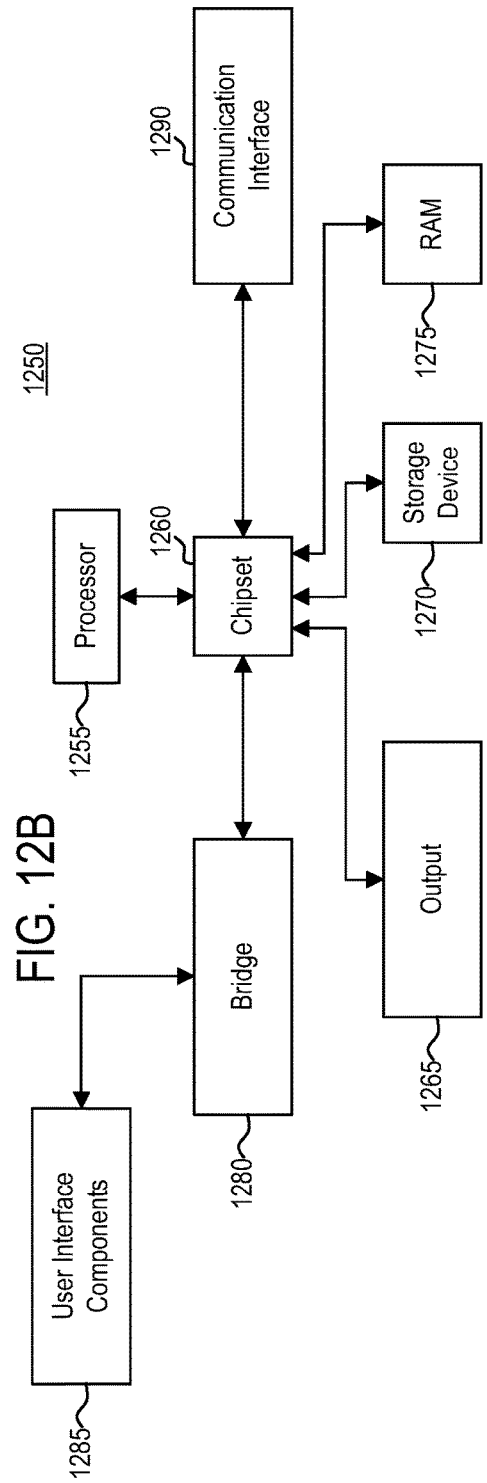
FIG. 12B is a block diagram illustrating a computing device, according to example embodiments.

FIG. 12B illustrates a computer system 1250 having a chipset architecture that may represent at least a portion of microprocessor 114 and/or blower controller 116. Computer system 1250 may be an example of computer hardware, software, and firmware that may be used to implement the disclosed technology. System 1250 may include a processor 1255, representative of any number of physically and/or logically distinct resources capable of executing software, firmware, and hardware configured to perform identified computations. Processor 1255 may communicate with a chipset 1260 that may control input to and output from processor 1255. In this example, chipset 1260 outputs information to output 1265, such as a display, and may read and write information to storage device 1270, which may include magnetic media, and solid state media, for example. Chipset 1260 may also read data from and write data to storage device 1275 (e.g., RAM). A bridge 1280 for interfacing with a variety of user interface components 1285 may be provided for interfacing with chipset 1260. Such user interface components 1285 may include a keyboard, a microphone, touch detection and processing circuitry, a pointing device, such as a mouse, and so on. In general, inputs to system 1250 may come from any of a variety of sources, machine generated and/or human generated.

Chipset 1260 may also interface with one or more communication interfaces 1290 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 1255 analyzing data stored in storage device 1270 or storage device 1275. Further, the machine may receive inputs from a user through user interface components 1285 and execute appropriate functions, such as browsing functions by interpreting these inputs using processor 1255.

It may be appreciated that example systems 1200 and 1250 may have more than one processor 1210 or be part of a group or cluster of computing devices networked together to provide greater processing capability.

While the foregoing is directed to embodiments described herein, other and further embodiments may be devised without departing from the basic scope thereof. For example, aspects of the present disclosure may be implemented in hardware or software or a combination of hardware and software. One embodiment described herein may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory (ROM) devices within a computer, such as CD-ROM disks readably by a CD-ROM drive, flash memory, ROM chips, or any type of solid-state non-volatile memory) on which information is permanently stored; and (ii) writable storage media (e.g., floppy disks within a diskette drive or hard-disk drive or any type of solid state random-access memory) on which alterable information is stored. Such computer-readable storage media, when carrying computer-readable instructions that direct the functions of the disclosed embodiments, are embodiments of the present disclosure.

It will be appreciated to those skilled in the art that the preceding examples are exemplary and not limiting. It is intended that all permutations, enhancements, equivalents, and improvements thereto are apparent to those skilled in the art upon a reading of the specification and a study of the drawings are included within the true spirit and scope of the present disclosure. It is therefore intended that the following appended claims include all such modifications, permutations, and equivalents as fall within the true spirit and scope of these teachings.

The invention claimed is:

1. A positive airway pressure device, comprising:
   a housing comprising:
      a blower disposed in the housing;
      a patient connection port formed in the housing, the patient connection port configured to selectively interface with a patient delivery system;

a chamber disposed in the housing, the chamber configured to receive gas generated by the blower and output the gas to a patient via the patient connection port;

a sensor at least partially disposed in the housing in a gas pathway between the blower and the patient connection port, the sensor configured to measure a pressure in the chamber; and a controller disposed in the housing, the controller in communication with the blower and the sensor, the controller configured to perform operations, comprising:

determining a baseline respiratory response for the patient by collecting, via the sensor, respiratory response data from the patient for a plurality of pressure levels, the determining comprising:

initializing the blower to deliver a first therapy pressure to the patient, collecting, from the sensor, a first set of respiratory response data corresponding to the first therapy pressure, initializing the blower to deliver a second therapy pressure to the patient, the second therapy pressure higher than the first therapy pressure, collecting, from the sensor, a second set of respiratory response data corresponding to the second therapy pressure, and analyzing the first set of respiratory response data and the second set of respiratory response data to identify the baseline respiratory response for the patient;

initializing the blower to deliver a therapy pressure to the patient;

receiving, from the sensor, real-time respiratory response data while delivering therapy to the patient;

analyzing the real-time respiratory response data to determine whether a sleep disruption has occurred by comparing the real-time respiratory response data to the baseline respiratory response for the patient;

based on the analyzing, determining that a sleep disruption has occurred based on an anomaly detected in the real-time respiratory response data; and based on the determining, initiating an action to account for the sleep disruption.

2. The positive airway pressure device of claim 1, wherein the initializing the blower to deliver the first therapy pressure and the initializing the blower to deliver the second therapy pressure are performed when the patient is sleeping or awake.

3. The positive airway pressure device of claim 1, wherein initiating the action to account for the sleep disruption comprises:

generating a control signal that causes the blower to adjust the therapy pressure delivered to the patient.

4. The positive airway pressure device of claim 3, further comprising:

delivering the adjusted therapy pressure to the patient.

5. The positive airway pressure device of claim 4, further comprising:

receiving, from the sensor, updated real-time respiratory response data while delivering the adjusted therapy pressure to the patient;

analyzing the updated real-time respiratory response data to determine whether a second sleep disruption has occurred by comparing the updated real-time respiratory response data to the baseline respiratory response for the patient;

based on the analyzing, determining that a second sleep disruption has not occurred; and based on the determining, continuing to deliver the adjusted therapy pressure to the patient.

6. The positive airway pressure device of claim 1, wherein initiating the action to account for the sleep disruption comprises:

generating an alert that notifies a clinician computing device of the sleep disruption; and sending the alert to the clinician computing device over one or more networks, the clinician computing device not co-located with the positive airway pressure device.

7. The positive airway pressure device of claim 1, wherein analyzing the real-time respiratory response data to determine whether the sleep disruption has occurred comprises:

comparing the real-time respiratory response data to one or more of a baseline frequency of respiration, a baseline amplitude of respiration, and a baseline shape of a baseline respiratory response curve.

8. A method for detecting a sleep disruption using a positive airway pressure device, the method comprising:

initializing a positive airway pressure device, the positive airway pressure device having a housing comprising a blower, chamber, sensor, and controller disposed therein, the sensor at least partially disposed in a gas pathway between the blower and a patient connection port formed in the housing, the patient connection port configured to selectively interface with a patient delivery system;

determining, by the controller of the positive airway pressure device, a baseline respiratory response for a patient by collecting, via the sensor, respiratory response data from the patient for a plurality of pressure levels, the determining comprising:

initializing the blower to deliver a first therapy pressure to the patient, collecting, from the sensor, a first set of respiratory response data corresponding to the first therapy pressure, initializing the blower to deliver a second therapy pressure to the patient, the second therapy pressure higher than the first therapy pressure, collecting, from the sensor, a second set of respiratory response data corresponding to the second therapy pressure, and analyzing the first set of respiratory response data and the second set of respiratory response data to identify the baseline respiratory response for the patient;

initializing, by the controller, the blower of the positive airway pressure device to deliver a therapy pressure to the patient;

receiving, by the controller from the sensor, real-time respiratory response data while delivering therapy to the patient;

analyzing, by the controller, the real-time respiratory response data to determine whether a sleep disruption has occurred by comparing the real-time respiratory response data to the baseline respiratory response for the patient;

based on the analyzing, determining, by the controller, that a sleep disruption has occurred based on an anomaly detected in the real-time respiratory response data; and based on the determining, initiating, by the controller, an action to account for the sleep disruption.

9. The method of claim 8, wherein initiating, by the controller, the action to account for the sleep disruption comprises:
- generating a control signal that causes the blower to adjust the therapy pressure delivered to the patient.

10. The method of claim 9, further comprising:
- delivering, by the controller, the adjusted therapy pressure to the patient.

11. The method of claim 10, further comprising:
- receiving, by the controller from the sensor, updated real-time respiratory response data while delivering the adjusted therapy pressure to the patient;
- analyzing, by the controller, the updated real-time respiratory response data to determine whether a second sleep disruption has occurred by comparing the updated real-time respiratory response data to the baseline respiratory response for the patient;
- based on the analyzing, determining, by the controller, that a second sleep disruption has not occurred; and
- based on the determining, continuing, by the controller, to deliver the adjusted therapy pressure to the patient.

12. The method of claim 8, wherein initiating, by the controller, the action to account for the sleep disruption comprises:
- generating an alert that notifies a clinician computing device of the sleep disruption, and
- sending the alert to the clinician computing device over one or more networks, the clinician computing device not co-located with the positive airway pressure device.

* * * * *